United States Patent
Madabhushi et al.

(10) Patent No.: US 9,262,583 B2
(45) Date of Patent: Feb. 16, 2016

(54) IMAGE SIMILARITY-BASED FINITE ELEMENT MODEL REGISTRATION

(71) Applicant: Case Western Reserve University, Cleveland, OH (US)

(72) Inventors: Anant Madabhushi, Beachwood, OH (US); Robert Toth, Long Valley, NJ (US)

( * ) Notice: Subject to any disclaimer, the term of this patent is extended or adjusted under 35 U.S.C. 154(b) by 64 days.

(21) Appl. No.: 14/225,850

(22) Filed: Mar. 26, 2014

(65) Prior Publication Data

US 2014/0294271 A1 Oct. 2, 2014

Related U.S. Application Data

(60) Provisional application No. 61/806,578, filed on Mar. 29, 2013.

(51) Int. Cl.
| | | |
|---|---|---|
| G06K 9/00 | (2006.01) | |
| G06F 19/00 | (2011.01) | |
| G06T 7/00 | (2006.01) | |
| G01R 33/56 | (2006.01) | |
| G06K 9/46 | (2006.01) | |
| G06K 9/62 | (2006.01) | |

(52) U.S. Cl.
CPC .......... *G06F 19/321* (2013.01); *G01R 33/5608* (2013.01); *G06F 19/3431* (2013.01); *G06K 9/0014* (2013.01); *G06K 9/00147* (2013.01); *G06K 9/4671* (2013.01); *G06K 9/6256* (2013.01); *G06T 7/0014* (2013.01); *G06T 7/0032* (2013.01); *G06T 7/0083* (2013.01); *G06T 7/0087* (2013.01); *G06T 2207/30081* (2013.01)

(58) Field of Classification Search
CPC ................ G06T 7/0014; G06T 7/0032; G06T 2207/30081; G06T 7/0083; G06T 7/0087; G01R 33/5608; G06K 9/4671; G06K 9/6256; G06K 9/0014; G06K 9/00147; G06F 19/321; G06F 19/3431
USPC ........................................................ 382/131
See application file for complete search history.

(56) References Cited

PUBLICATIONS

Crouch et al., "Automated Finite Element Analysis for Deformable Registration of Prostate Images", Oct. 2007, Retrieved from Internet on Jul. 22, 2015 from <URL:http://midag.cs.unc.edu/pubs/papers/TMI-Prostate-Jan07.pdf>.*

(Continued)

*Primary Examiner* — Gregory F Cunningham

(57) ABSTRACT

Apparatus, methods, and other embodiments associated with evaluating global deformations and local deformations in a prostate are described. One example apparatus includes logics that evaluate global and local deformations in a prostate and register a pre-External Beam Radiation Treatment (EBRT) three dimensional (3D) magnetic resonance (MR) image with a post-EBRT 3D MR image. An image acquisition logic acquires a pre-EBRT image and a post EBRT image of an organ, item, or volume. An image texture information logic extracts image texture information from the pre-EBRT and post-EBRT images. A finite element model (FEM) transformation logic constructs a FEM of the volume imaged in the pre-EBRT image, deforms the FEM, deforms the pre-EBRT image as a function of the deformed FEM, and maximizes the image texture similarity between the deformed pre-EBRT image and the post-EBRT image. A registration logic registers the pre-EBRT image with the post-EBRT image based on the transformation.

21 Claims, 6 Drawing Sheets

(56) References Cited

PUBLICATIONS

Robert Toth, "Evaluating Treatment Related Changes for Prostate Cancer Via Image Analysis Tools and Magnetic Resonance Imaging", Jan. 2014, Retrieved on Jul. 22, 2015 from Internet <URL:https://rucore.libraries.rutgers.edu/rutgers-lib/42464/PDF/1/>.*

Jeffrey F. Williamson, "Integration of IMRT and Brachytherapy", 2006, Retrieved on Jul. 22, 2015 from Internet <URL:eknygos.Ismuni.It/springer/211/423-437.pdf>.*

David Sarruttex, "Deformable Registration for Image-Guided Radiation Therapy", Mar. 30, 2006, Retrieved on Jul. 22, 2015 from Internet <URL:http://www.creatis.insa-lyon.fr/~dsarrut/mybib/2006/sarrut-zmedphys2006-long-version/>.*

V.R.S Mani, "Survey of Medical Image Registration", Jan. 1, 2013, Retrieved on Jul. 24, 2015 from Internet <URL:http://www.sciepub.com/portal/downloads?doi=10.12691/jbet-1-2-1&filename=jbet-1-2-1.pdf>.*

Walter Frei, "Solutions to Linear Systems of Equations: Direct and Iterative Solvers", Nov. 13, 2013, Retreived on Jul. 24, 2015 from Internet <URL:http://www.comsol.com/blogs/solutions-linear-systems-equations-direct-iterative-solvers/>.*

Alterovitz et al., "Registration of MR prostate images with biomechanical modeling and nonlinear parameter estimation", Feb. 2006, Retrieved from Internet on Jul. 22, 2015 from <URL:http://goldberg.berkeley.edu/pubs/Registration-MedPhys.pdf>.*

Goksel, "Ultrasound Image and 3D Finite Element based Tissue Deformat ion Simulator for Prostate Brachytherapy", Dec. 2004, Retrieved from Internet on Jul. 22, 2015 from <URL:https://circle.ubc.ca/bitstream/id/39114/ubc_2005-0045.pdf>.*

\* cited by examiner

IMAGE SIMILARITY-BASED FINITE ELEMENT MODEL REGISTRATION

CROSS REFERENCE TO RELATED APPLICATIONS

This application claims the benefit of U.S. Provisional Application No. 61/806,578 filed on Mar. 29, 2013.

BACKGROUND

External Beam Radiation Treatment (EBRT) for cancer involves irradiating an organ, tissue, or other region with ionizing radiation. EBRT changes the organ, tissue, or region and these changes may appear in magnetic resonance (MR) imagery of the treated organ, tissue, or region. Cancer treatment may be evaluated by detecting changes at the voxel-level in MR images of the treated organ, tissue, or region. Changes in pre-EBRT and post-EBRT images may be correlated with recurrence and complete or partial response to the EBRT. Quantifying the changes on a voxel-level involves spatially aligning, or registering, the pre-EBRT and post-EBRT MR images. However, little is known about specific changes to treated material as a function of EBRT. In one example, following EBRT, there is significant shrinkage and compression, as well as non-linear deformation, of the prostrate. Other treated regions may show other deformations. Registering pre-EBRT and post-EBRT MR images may be challenging due to the non-linear deformation, shrinkage or other changes, which may require using an elastic registration technique to achieve desired registration. Conventional registration methods employ simple linear registrations, including rigid registration, which may produce sub-optimal results. For example, inaccuracies in conventional registration of pre-EBRT and post-EBRT images may result in sub-optimal assessment of the changes to the treated area caused by the EBRT.

A Finite Element Model (FEM) in the context of EBRT and MR is a model that describes tissue properties including compressibility and elasticity. FEMs have traditionally been parameterized by a collection of finite elements such as tetrahedrons or hexahedrons connected at nodes. The material properties of elements define how a force at one node affects other nodes. FEMs have been employed to determine how a set of external forces displace tissue. Conventionally, FEMs have been employed to capture the motion of the various tissues on computed tomography (CT) imagery of cancer patients. Capturing this motion facilitates exploring different material properties for benign tissue, tumors, and benign afflictions such as prostatic hyperplasia. Chi et al., *A material sensitivity study on the accuracy of deformable organ registration using linear biomechanical models*, Med. Phys., vol. 33, no. 2, pp 421-433, February 2006. Similarly, FEMs model bladder, prostate, and rectum movement on CT imagery, with the results compared to a cadaver. Boubaker et al., *Finite element simulation of interactions between pelvic organs: Predictive model of the prostate motion in the context of radiotherapy*, J. Biomech., vol. 42, pp. 1862-1868, 2009. Other conventional registration methods calculate a medial axis between the fixed and moving images, and displace the FEM nodes based on an alignment of the medial axes. Crouch et al., *Automated finite-element analysis for deformable registration of prostate images*, IEEE TMI, vol. 26, no. 10, pp. 1379-1391, October 2007. The displacements are used as boundary conditions, and the FEM is used to calculate the displacement of the entire gland.

Conventional methods employ the alignment of the femoral heads for an initial rigid registration, after which the displacements between nodes on the organ surface are used as boundary conditions. For example, Hensel et al. used a FEM to register MR imagery acquired with an endorectal coil to MR imagery acquired without the endorectal coil. Hensel et al., *Development of multiorgan finite element-based prostate deformation model enabling registration of endorectal coil magnetic resonance imaging for radiotherapy planning*, Int. J. of Rad. Onc. Bio. Phys., vol. 68, no. 5, pp. 1522-1528, 2007. Conventionally, MR image to MR image registration involved calculating nodes on the surface of the prostate. The nodes are used as boundary conditions for an FEM that calculates deformations and forces. Brock et al., *Accuracy and sensitivity of finite element model-based deformable registration of the prostate*, Med. Phys., vol. 35, no. 9, pp. 4019-4025, September 2008.

Conventional FEM-based registration frameworks align nodes of one surface onto the nodes of another surface, typically using the Iterative Closest Points (ICP) algorithm. However, conventional methods assume that the node correspondences can be accurately determined. Furthermore, conventional FEM-based registration methods require the surfaces to be aligned, with no consideration of the imaging information. Conventional FEMs tend to focus on how external forces affect the surfaces and assume that the gland is a volume-preserving entity. Conventional methods therefore have sub-optimal accuracy when assessing early EBRT effectiveness, and when determining if early intervention in case of incomplete disease response to the EBRT is required.

BRIEF DESCRIPTION OF THE DRAWINGS

The accompanying drawings, which are incorporated in and constitute a part of the specification, illustrate various example systems, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Figure 1:
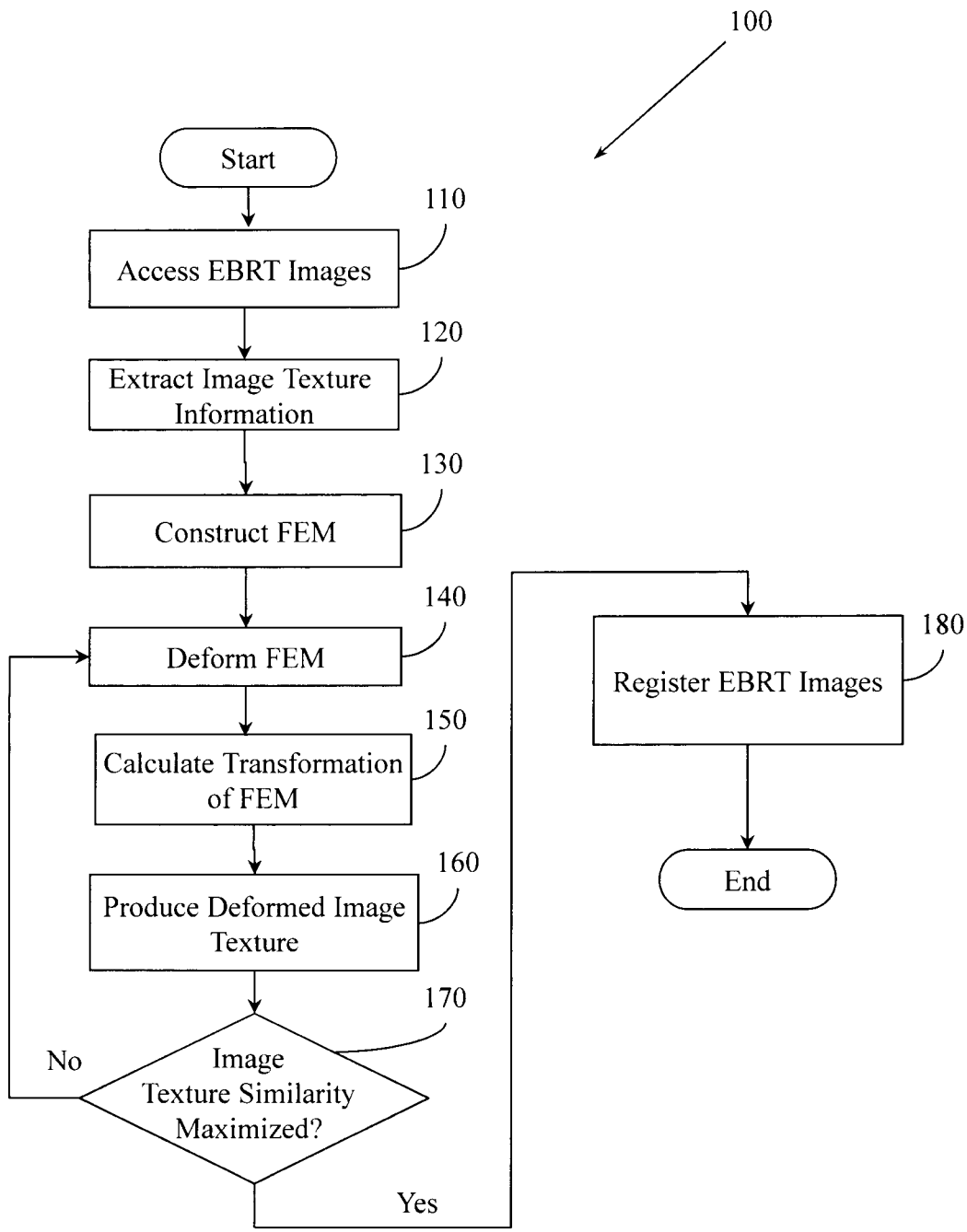
FIG. 1 illustrates an example method of evaluating global deformations and local deformations in a prostate due to effects of External Beam Radiation Treatment (EBRT) in a prostate cancer patient.

Conventional systems for registering pre-EBRT and post-EBRT MR images using FEMs have relied on rigid initial registration and have involved aligning nodes of one surface onto corresponding nodes of another surface. Conventional systems have assumed that node correspondence can be accurately determined. Furthermore, in conventional systems the surfaces of the prostate must be aligned, with no consideration of the imaging information. Manual registration is time-consuming and unsuitable for large-scale studies, and may be prone to errors and inter-observer variability. Thus, conventional systems, both manual and FEM-based, result in inaccurate registration that limits usefulness in assessing the effectiveness of EBRT. Example systems, apparatus, and methods quantitatively evaluate image related changes in a post-EBRT organ, tissue, or region and evaluate more precise global and local deformations in the organ, tissue, or region due to effects of radiation.

Example systems, apparatus, and methods employ a texture based finite element model (FEM) registration scheme to register pre-EBRT and post-EBRT images of a prostate, tissue region, or material. Example systems, apparatus, and methods construct a FEM of the item depicted in the pre-EBRT image. The FEM captures the surface of the item and the internal architecture of the item organ. Example systems, apparatus, and methods extract image texture information from a pre-EBRT image and a post-EBRT image, and, using the FEM depicted in the pre-EBRT image, deform the FEM until the mutual information between a texture transformation of the pre-EBRT image and the post-EBRT image is maximized. Example systems, apparatus, and methods employ a biconjunctive gradient stabilized method to estimate the displacement of nodes in the deformed FEM, thereby reducing the computational cost of solving the deformed FEM. Example systems, apparatus, and methods may employ a particle swarm based optimization technique to determine which forces applied to the FEM will result in the greatest texture similarity.

EBRT changes the item and these changes are recorded in the post-EBRT image. By maximizing the similarity between the post-EBRT image texture and the deformed pre-EBRT image, based on the FEM, example systems, apparatus, and methods objectively quantify the changes in the item. Objectively quantifying the changes in the item facilitate accurate registration of the pre-EBRT and post-EBRT images in a clinically relevant timeframe. Example systems, apparatus, and methods thus improve on conventional methods when determining whether early intervention in case of incomplete disease response to the EBRT is required.

EBRT for cancer involves irradiating an area or item with ionizing radiation. The ionizing radiation is applied with the aim of destroying cancerous cells. However, little is known about specific changes in the area or item that are caused by EBRT. Even though little is known about the specific changes, changes to the area or item caused by EBRT may appear as changes on MR images. These changes may be quantified by spatially aligning, or registering, the pre-EBRT and post-EBRT images. However, following EBRT, the area or item may undergo significant shrinkage, compression, and non-linear deformations, which may complicate registration. While pre-EBRT and post-EBRT images have been registered manually, computerized methods have been employed to avoid human error and inter-reviewer variability. Conventional computerized methods have employed simple, linear registration techniques, including rigid registration involving translation and rotation. However, elastic registration that accounts for the shrinkage, compression, and non-linear deformations provides more accurate registration results than conventional methods. Example systems, apparatus, and methods facilitate determining pixel-by-pixel changes in post-EBRT images, and facilitate determining more precise local deformations to the item or area or other cancerous regions by spatially registering the pre-EBRT and post-EBRT images based on image texture, rather than merely aligning surface nodes. Example systems, apparatus, and methods employ an FEM to facilitate registering the pre-EBRT and post-EBRT images.

Finite element models, with respect to prostate or other cancer treatment, are models that describe certain tissue properties, including compressibility and elasticity. FEMs have been used to determine how a set of external forces can displace tissue. FEMs are conventionally parameterized by a collection of finite elements. These finite elements may include geometric shapes including tetrahedrons or hexahedrons. The elements of an FEM are connected at nodes. Elements comprise material properties. The material properties of each node define how a force at one node affects other nodes. Conventional methods of registering pre-EBRT and post-EBRT images using FEMs relied on aligning nodes on the surface of the area or item, which assumes the node correspondences can be accurately determined. Example systems, apparatus, and methods register the pre-EBRT and post-EBRT images by maximizing the image texture similarity between the pre-EBRT and post-EBRT images, rather than the conventional method of aligning surface nodes. Example systems, apparatus, and methods, by employing image texture similarity rather than merely aligning surface nodes, allow for more accurate alignment of internal structures of the item or area that may have been displaced as a result of the EBRT. Example systems, apparatus, and methods achieve a mean root mean square (RMS) error between manually selected fiducials visible on both pre-EBRT and post-EBRT images of 2.99 mm. Example systems, apparatus, and methods thus achieve a statistically significant improvement over surface-based registration, which has an RMS of 5.07 mm, and affine registration, which achieved an RMS of 3.42 mm between manually selected fiducials visible on both pre-EBRT and post-EBRT prostate images.

An FEM discretizes a problem into elements in order to numerically solve for the deformation of a continuous body. Elements of the FEM represent a geometric shape. For example, one FEM may discretize a problem into elements, where elements represent a tetrahedron, defined by four corner nodes. In another FEM, an element may represent a hexahedron, defined by eight corner nodes. Elements of an FEM contain physical properties. An FEM element may contain elasticity, as defined by Young's modulus, and compressibility, expressed by Poisson's ratio. Other physical properties, including mass, may be modeled into the FEM elements.

Consider an example three dimensional (3D) FEM. The 3D FEM has a number of nodes N, N being an integer. A 3N×3N sparse, symmetric stiffness matrix K defines how nodes in the FEM interact with the other nodes in other dimensions. A 3N×1 vector V represents the coordinates of the nodes in each of the three dimensions. A 3N×1 vector F represents a series of external forces applied to the nodes in each dimension. A 3N×1 vector U represents the displacement of the nodes in each dimension. The (x, y, z) displacement of node $n \in \{1, \ldots, N\}$ is defined as $u_n \in \mathbb{R}^3$. The (x, y, z) coordinates of node $n \in \{1, \ldots, N\}$ are defined as $v_n \in \mathbb{R}^3$. The (x, y, z) force at node $n \in \{1, \ldots, N\}$ is similarly defined as $f_n \in \mathbb{R}^3$.

FEM modelling seeks to determine the displacement of nodes given a collection of external forces applied to the object modelled by the FEM. Determining the displacement of nodes is conventionally accomplished by solving $K \cdot U = F$ for U. However, solving $U = K^{-1} \cdot F$ directly is computationally infeasible. Iterative algorithms have been employed to estimate U. Example systems, apparatus, and methods employ the biconjugate gradient stabilized method (BiCGSTAB) to estimate U by minimizing $\|F-K \cdot U\|_2$. After solving for U, the deformed nodes $V' \in \mathbb{R}^{3N}$ are calculated as $V'=V+U$. Example systems, apparatus, and methods therefore solve the FEM in a clinically relevant timeframe by estimating U. Other methods of estimating U may be employed to solve the FEM in a clinically relevant timeframe.

Example systems, apparatus, and methods register a pre-EBRT MR image to a post-EBRT MR image. The pre-EBRT image $C_{Pre}$ and post-EBRT image $C_{Post}$ comprise a collection of voxels and image texture information about the voxels. An image scene $C=\{C,f\}$ may be defined by a collection of voxels $c=(x,y,z)$, $\forall c \in C$, and texture information for each voxel $f(c) \in \mathbb{R}$, $\forall c \in C$. Example systems, apparatus, and methods control a computer to calculate a transformation T such that $T=\arg \max E(C_{Post}, T(C_{Pre}))$, where $T(C_{Pre})=\{C_{Pre}, f_{Pre}(T(c))\}$ represents the transformed pre-EBRT image. In mathematics, arg max is the argument of the maximum, which is defined as the set of points of the given argument for which the given function attains its maximum value.

$$\arg\max_x f(x) := \{x \mid \forall y : f(y) \leq f(x)\}$$

In other words, arg max, f(x) is the set of values of x for which f(x) attains its largest value M. For example, if f(x) is $1-|x|$, then it attains its maximum value of 1 at x=0 and only there, so arg max, $(1-|x|)=\{0\}$. The parameterization of the transformation T is defined by a series of M non-zero external forces on the surface of the item or area represented in the FEM comprising F, where M≤N. While conventional registration methods align a series of fiducials on the surface of the object of interest, example systems, apparatus, and methods use the image texture information to drive the registration, rather than surface points. Example systems, apparatus, and methods maximize the image energy E, which is defined as the mutual information between a texture transformation of the pre-EBRT image and the post-EBRT image. In one embodiment, a sobel image gradient is employed.

Example systems, apparatus, and methods define the FEM transformation of the entire pre-EBRT image from the resulting displacements U, given the non-zero external forces F. The nodes surrounding a voxel c, $S_c \subset \{1, \ldots, N\}$, are defined by the corners of the FEM element containing c. In one embodiment where the FEM comprises tetrahedron elements, $S_c \in \mathbb{R}^4$. In another example where the FEM comprises hexahedron elements, then $S_c \in \mathbb{R}^8$. FEM elements may comprise geometric shapes other than tetrahedrons and hexahedrons, and $S_c$ may be defined in dimensions other than four or eight. Determining the displacements U facilitates defining the transformation of the voxels in the pre-EBRT image. The transformation of the voxel c is defined as a linear interpolation of the nodal displacements $$T(c) = c + \frac{\sum_{n \in S_c} \|c - v_n\|_2 \cdot u_n}{\sum_{n \in S_c} \|c - v_n\|_2}.$$

In example systems, apparatus, and methods, the transformation T has 3M degrees of freedom, where $f_n \in \mathbb{R}^3$ for each external force. Although example systems, apparatus, and methods may involve three dimensions, the transformation T may have other degrees of freedom depending on the dimension of the vector space. The 3M parameters defining T may be modified and a determination of which external forces F maximize the image similarity energy may be made. The external forces F that maximize the image similarity energy are found by solving $T=\arg \max E(C_{Post}, T(C_{Pre}))$. A particle swarm optimizer may determine which external forces maximize the image similarity. In one embodiment, one hundred random parameters, also referred to as particles, are allowed to converge independently on the maximum energy E. The particle with the maximum energy overall is chosen. One example of a particle swarm optimizer is described in Wachowiak et al., *An approach to multimodal biomedical image registration using particle swarm optimization*, IEEE TEC, vol. 8, no. 3, pp. 289-301, 2004. Other optimizers and associated parameters may be employed in other embodiments.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, determining, and so on, refer to actions and processes of a computer system, logic, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

FIG. 1 illustrates a computerized method 100 of evaluating global deformations and local deformations in a prostate due to effects of External Beam Radiation Treatment (EBRT). While a prostate is described, more generally, example methods may evaluate global deformation and local deformations in a cancerous region. Method 100 includes, at 110, accessing a three dimensional (3D) pre-EBRT magnetic resonance (MR) image of a prostate. The pre-EBRT image comprises a first set of voxels and first image texture information about the first set of voxels. Method 100, at 110, also includes accessing a 3D post-EBRT MR image of the prostate. The post-EBRT image comprises a second set of voxels and second image texture information about the second set of voxels. Accessing the pre-EBRT and post-EBRT images may include, for example, acquiring data from a medical imaging apparatus, receiving data via a computer network, receiving data through a function call, or other computer based operation. In one embodiment, the pre-EBRT image and post-EBRT image are T2-weighted MRI. In one embodiment, the T2-weighted MRI may be acquired using a 1.5 Tesla GE MRI scanner or a 3.0 Tesla GE MRI scanner. In one embodiment, the size of the pre-EBRT and post-EBRT images are approximately 140× 140×140 mm. The voxel sizes may range from 0.27×0.27×2.2 mm/voxel to 0.54×0.54×3.0 mm/voxel. In other embodiments, other MRI scanners may be used, other sizes of pre-EBRT and post-EBRT images may be acquired, and other voxel sizes may be employed.

Method 100 also includes, at 120, extracting first image texture information from the pre-EBRT image and extracting second image texture information from the post-EBRT image. Extracting the image texture information may include, for example, manually delineating an organ surface and other structures on each image using Slicer software, or automatically delineating an organ and other structures. While an organ is described, more generally an item or volume may be processed.

Method 100 also includes, at 130, constructing a finite element model (FEM) of the pre-EBRT image. In one embodiment, the FEM discretizes structures of the organ into elements of the FEM. The elements of the FEM represent a geometric shape, and the elements of the FEM contain physical properties including elasticity or compressibility. In one embodiment, the elements of the FEM may contain physical properties in addition to or in place of elasticity and compressibility, including mass. The elements of the FEM are connected at nodes of the FEM. In one embodiment, the FEM is a 3D FEM. The 3D FEM comprises a plurality of nodes N. The elements of the 3D FEM represent a tetrahedron or a hexahedron. A tetrahedron is defined by four corner nodes, and a hexahedron is defined by eight corner nodes. In another embodiment, the elements of the 3D FEM may represent geometric shapes that are defined by a different number of corner nodes.

Method 100 also includes, at 140, producing a deformation of the FEM by applying a series of non-zero external forces to the surface of the organ represented by the FEM. In one embodiment, interaction of nodes in three dimensions is defined by a 3N×3N matrix K. K may be a sparse, symmetrical matrix. In one embodiment, a 3N×1 vector V represents the co-ordinates of the nodes in three dimensions. The series of non-zero external forces is denoted by M, where a 3N×1 vector F represents the series of non-zero external forces M applied to a node in three dimensions. M is less than or equal to the number of nodes N. The displacement of nodes in three dimensions by the series of non-zero external forces is represented by a 3N×1 vector U. In another embodiment, a series of non-zero internal forces are applied to internal structures of the organ modelled in the FEM. For example, forces may be applied to the central gland (CG) and peripheral zone (PZ) internal regions of the prostate modelled in the FEM, in addition to forces applied at the surface.

Method 100 also includes, at 150, calculating a transformation of the FEM, based at least in part, on the deformation. The transformation is parameterized based on the series of non-zero external forces applied to the surface of the prostate. In one embodiment, the displacement of nodes in the FEM by the series of non-zero external forces is computed according to $U = K^{-1} \cdot F$. U is estimated using a biconjugate gradient stabilized method by minimizing $\|F - K \cdot U\|_2$. After solving for U, the deformed nodes V' are calculated as $V' = V + U$. In one embodiment, the transformation is defined from the displacement of the nodes in the FEM. Nodes $S_c$ surrounding a voxel c in the first set of voxels are defined by corners of an element of the FEM, where the element contains the voxel c.

Method 100 also includes, at 160, producing a deformed first image texture by deforming, as a function of the deformation of the FEM, the first image texture. In one embodiment, the transformation T of the voxel c has 3M degrees of freedom. T is defined as a linear interpolation of the displacement of the nodes $S_c$. The transformation T is expressed as $$T(c) = c + \frac{\sum_{n \in S_c} \|c - v_n\|_2 \cdot u_n}{\sum_{n \in S_c} \|c - v_n\|_2}.$$

In this example, $u_n$ denotes displacement of a node n as described by the 3N×1 vector U, and $v_n$ denotes coordinates of a node n as described by the 3N×1 vector V.

Method 100 also includes, at 170, determining, as a function of the transformation, a non-zero external force that maximizes an image texture similarity between the deformed first image texture and the second image texture. Method 100 also includes, at 180, registering the pre-EBRT image to the post-EBRT image based, at least in part, on the transformation. In one embodiment, registering the pre-EBRT image to the post-EBRT image comprises calculating T=arg max $E(C_{Post}, T(C_{Pre}))$, where $T(C_{Pre}) = \{C_{Pre}, f_{Pre}(T(c))\}$. In this embodiment, $C_{Pre}$ represents the pre-EBRT image, and $C_{Post}$ represents the post-EBRT image. Image texture information for a voxel is denoted by $f_{pre}$. Image energy is denoted by E. The image energy is defined as mutual information between a texture transformation of the pre-EBRT image and the post-EBRT image. From calculating T=arg max $E(C_{Post}, T(C_{Pre}))$, the deformed pre-EBRT image and the post-EBRT images are brought into spatial alignment. In one embodiment, registering the images may comprise displaying the spatially aligned images on a monitor, storing the registered images in a memory as a new registered image, or producing a physical copy of the registered images. In one embodiment, method 100 achieves a root mean square (RMS) error between manually selected fiducials visible on both pre-EBRT and post-EBRT images of 2.73 mm, which is a statistically significant improvement over conventional methods. Conventional surface-based registration achieved a RMS of 5.07 mm and affine registration achieved a RMS of 3.42 mm.

In one embodiment, method 100 employs, at 170, a particle swarm optimizer to determine a series of non-zero external forces that maximizes E. In another embodiment, other optimizers may be employed to determine the series of non-zero external forces that maximize E.

While FIG. 1 illustrates various actions occurring in serial, it is to be appreciated that various actions illustrated in FIG. 1 could occur substantially in parallel. By way of illustration, a first process could extract image texture information from a first image, a second process could extract image texture information from a second image, and a third process could construct an FEM of the organ depicted in the first image. While three processes are described, it is to be appreciated that a greater or lesser number of processes could be employed and that lightweight processes, regular processes, threads, and other approaches could be employed.

Figure 2:
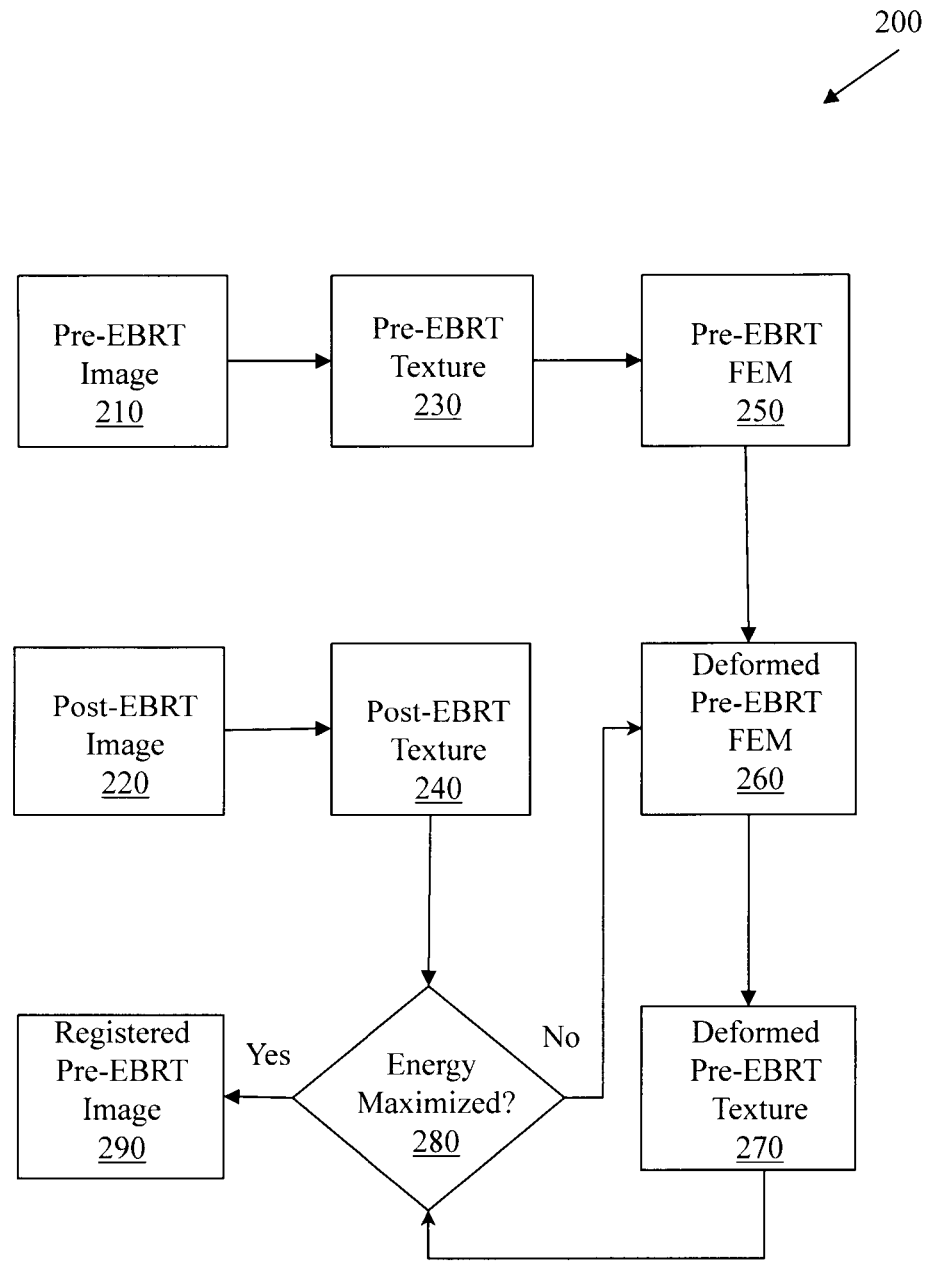
FIG. 2 illustrates an example implementation of a method for evaluating global deformations and local deformations in a prostate due to effects of EBRT in a CaP patient.

FIG. 2 is a flowchart of an example implementation of method 100. FIG. 2 illustrates at 210, a 3D pre-EBRT MR image of a prostate and at 220, a 3D post-EBRT image MR image of the prostate. At 230, pre-EBRT image texture information is extracted from the pre-EBRT image. At 240, post-EBRT image texture information is extracted from the post-EBRT image. FIG. 2 illustrates, at 250, the pre-EBRT FEM of the prostate constructed from the pre-EBRT image. The structures of the prostate are discretized into the FEM. At 260, FIG. 2 illustrates the deformation of the pre-EBRT FEM. At 270, FIG. 2 illustrates the deformation of the pre-EBRT image texture based on the deformation of the pre-EBRT FEM. At 280, FIG. 2 illustrates determining if the energy, defined as the mutual information between the texture transformation of the pre-EBRT image and the post-EBRT image, has been maximized. If the energy has not been maximized, FIG. 2 illustrates returning to deform the pre-EBRT FEM again at 260. In one embodiment, an optimizer iteratively induces different deformations until the similarity energy is maximized. In one embodiment, the optimizer is a particle swarm optimizer. In another embodiment, the optimizer is an optimizer other than a particle swarm optimizer. The optimizer may comprise a single optimizer, a combination of multiple optimizers of different types, or other optimizers. If, however, it is determined that the energy has been maximized, the pre-EBRT image is registered to the post-EBRT image at 290.

Figure 3:
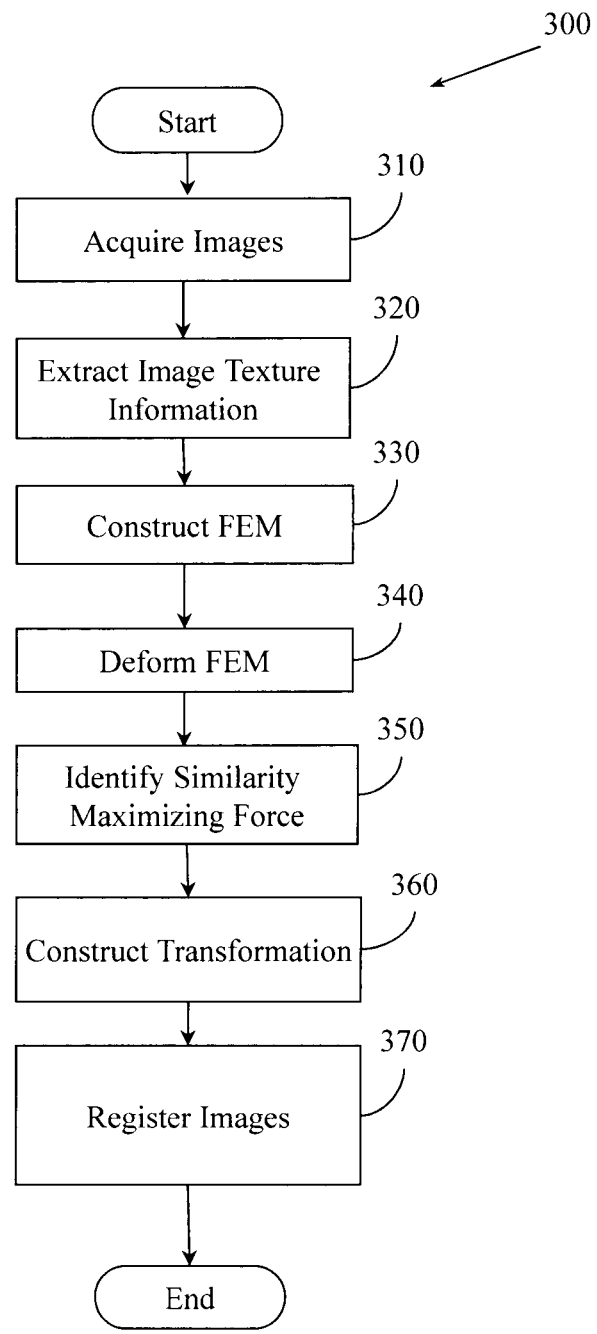
FIG. 3 illustrates an example method of registering a pre-Radiation Treatment (RT) image of an anatomical structure with a post-RT image of the anatomical structure.

FIG. 3 illustrates a method 300 associated with registering a pre-radiation treatment (RT) image of a region of tissue with a post-RT image of a region of tissue. Method 300 includes, at 310, acquiring a pre-RT image of an anatomical structure and a post-RT image of the anatomical structure. In one embodiment, the Radiation Treatment is an External Beam Radiation Treatment (EBRT). In one embodiment, the anatomical structure is a prostate. In another embodiment, the radiation treatment may be a form of radiation treatment other than EBRT such as Intensity Modulated Radiation Treatment (IMRT). In another embodiment, the anatomical structure may be a structure other than a prostate that is susceptible to radiation treatment.

Method 300 also includes, at 320, extracting first image texture information from the pre-RT image and extracting second image texture information from the post-RT image. In one embodiment, the pre-RT image and post-RT image are acquired using a 1.5 Tesla GE MRI scanner or a 3.0 Tesla GE MRI scanner. In one embodiment, the size of the pre-RT and post-RT images are approximately 140×140×140 mm and the voxel sizes range from 0.27×0.27×2.2 mm/voxel to 0.54× 0.54×3.0 mm/voxel. In other embodiments, other MRI scanners may be used, other sizes of pre-RT and post-RT images may be acquired, and other voxel sizes may also be employed.

Method 300 also includes, at 330, constructing an FEM of the anatomical structure in the pre-RT image. In one embodiment, the FEM discretizes structures of the region of tissue into elements that represent a geometric shape. The geometric shape represented by elements of the FEM may be a tetrahedron, a hexahedron, or other geometric shapes. The elements of the FEM contain physical properties that may include elasticity, compressibility, mass, or other physical properties. The elements of the FEM are connected at nodes. In one embodiment, the FEM is a 3D FEM that comprises a plurality of nodes.

Method 300 also includes, at 340, deforming the FEM of the anatomical structure in the pre-RT image to produce a deformation in the pre-RT image that maximizes the similarity between the first image texture information and the second image texture information. In one embodiment, the interaction of nodes is defined by a sparse, symmetrical matrix. The co-ordinates of the nodes in three dimensions are represented by a vector. Similarly, the series of non-zero external forces applied to a node in three dimensions is also represented by a vector. The series of non-zero external forces is less than or equal to the number of nodes in the FEM. The displacement of nodes in three dimensions by the series of non-zero external forces is also represented by a vector. In another embodiment, the FEM is deformed by a series of non-zero internal forces applied to internal structures of the prostate modelled in the FEM, in addition to the series of non-zero external forces.

Method 300 also includes, at 350, identifying an external force that maximizes the similarity of image texture information between the pre-RT image and the post-RT image. In one embodiment, method 300 may also include, at 350, identifying an internal force, or a combination of internal and external forces, that maximize the similarity of image texture information between the pre-RT image and the post-RT image. In another embodiment, method 300 may, at 350, identify an internal force, or a combination of internal and external forces, that maximize the similarity of other image information such as the degree of surface or internal structures' alignment. In one embodiment, method 300 may, at 350, employ a particle swarm optimizer to identify the external force that maximizes the similarity. In another embodiment, method 300 may employ an optimizer other than a particle swarm optimizer to identify the external force that maximizes the similarity.

Method 300 also includes, at 360, constructing a transformation of the FEM that achieves the deformation. In one embodiment, method 300 employs a linear interpolation of the displacement of the nodes to define the transformation. In another embodiment, method 300 may employ a non-linear interpolation of the displacement of the nodes to define the transformation.

Method 300 also includes, at 370, registering the pre-RT image with the post-RT image, based at least in part, on the transformation. In one embodiment, the registration of the pre-RT image with the post-RT image is driven by image texture of the organ, item, or volume. In another embodiment, the registration of the pre-RT image with the post-RT image is driven by additional image information besides texture, such as internal structures' alignment.

Figure 4:
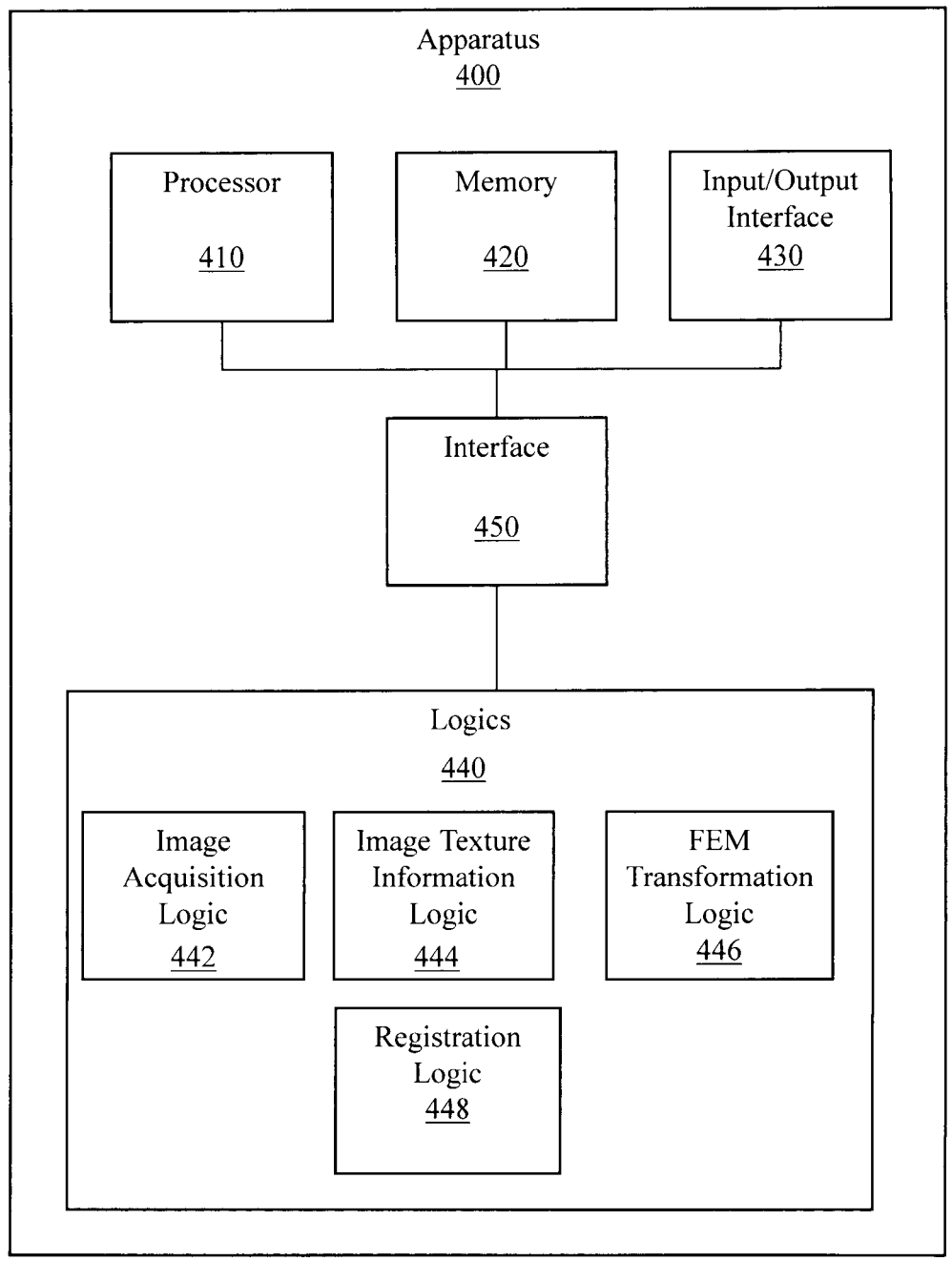
FIG. 4 illustrates an example apparatus that evaluates global deformations and local deformations in a region of tissue.

FIG. 4 illustrates an example apparatus 400. Apparatus 400 includes a processor 410, a memory 420, an input/output interface 430, a set of logics 440, and an interface 450 to connect the processor 410, the memory 420, the input/output interface 430, and the set of logics 440. The set of logics 440 evaluates global deformations and local deformations in an item or region. The global deformations and local deformations may be caused by the effects of a treatment applied to the item, region, or region of tissue. In one embodiment, the region of tissue is a prostate, and the global deformations and local deformations are cause by EBRT. In another embodiment, the region of tissue may be a region of tissue other than a prostate that is treated with EBRT. In another embodiment, a treatment other than EBRT is applied to the region of tissue.

The set of logics 440 evaluates global deformations and local deformations in the region of tissue and registers pre-RT and post-RT images. The set of logics 440 includes an image acquisition logic 442 that acquires two or more images of a tissue. The two or more images are acquired at different times. For example, a first image may be acquired before a patient undergoes RT and the second image may be acquired after the patient undergoes RT. In one embodiment, the images are 3D MRI images. In another embodiment, the images may be two dimensional images. In another embodiment, the images may be two or three dimensional non-MRI images.

The set of logics 440 also includes an image texture information logic 444 that determines a texture property of the two or more images of the tissue. In one embodiment, members of the two or more images include a set of voxels and image texture information about the set of voxels. In another embodiment, members of two or more images include image information about the voxels in addition to texture, such as internal structures' alignment.

The set of logics 440 also includes an FEM transformation logic 446 that computes a transformation for the two or more images using an FEM. FEM transformation logic 446 constructs an FEM of the first image and produces a deformed FEM by applying a non-zero force to the FEM. FEM transformation logic 446 calculates a displacement of nodes in the deformed FEM by generating a solution to the deformed FEM. Since solving the FEM directly is computationally infeasible, FEM logic 446 estimates the displacement of nodes in the FEM. In one embodiment, FEM logic 446 employs a biconjugate gradient stabilized method to estimate the displacement of nodes in the FEM. FEM transformation logic 446 produces a deformed first image based on the solution to the deformed FEM, and extracts a third image texture information from the deformed first image. FEM logic 446 then determines if the similarity between the third image texture information and the second image texture information is maximized. Upon determining that the similarity between the third image texture information and the second image texture information is maximized, FEM transformation logic 446 determines which non-zero force maximizes the similarity and computes a transformation of the first image that achieves the deformed first image.

The set of logics 440 includes a registration logic 448 that registers the two or more images using the transformation. Registering, as used herein, refers to its usage in computer imaging and medical imaging. Thus, image registration may include transforming different sets of data into one co-ordinate system. Registering images facilitates comparing or integrating data from different images. In one embodiment, registration comprises bringing the deformed pre-RT MR image into spatial alignment with the post-RT MR image. Registration facilitates voxel-by-voxel examination of imaging related changes caused by the RT. For example, a plurality of fiducials corresponding to structures in the item or region of tissue may be identified in the pre-RT image and in the post-RT image. The RMS displacement between the fiducials in the deformed pre-RT image and the post-RT image may then be calculated to assess the accuracy of the registration.

Figure 5:
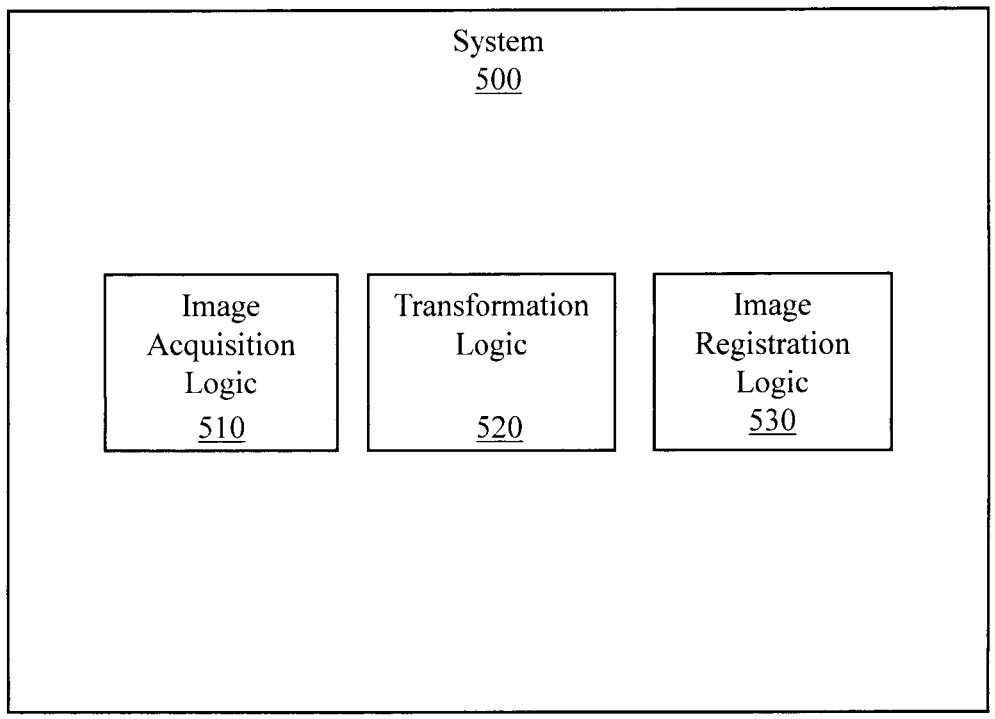
FIG. 5 illustrates an example system that evaluates global deformations and local deformations in a material.

FIG. 5 illustrates an example system 500 associated with registering a first image with a second image. Embodiments of system 500 may be employed to evaluate deformations in a region of a material in which pre-deformation and post-deformation images of the material are to be registered. System 500 includes an image acquisition logic 510 that provides means for receiving digitized image data. System 500 also includes a transformation logic 520 that provides means for evaluating global deformations and local deformations in a material so that image texture similarity between a first image and a second image is maximized. System 500 also includes a registration logic 530 that provides means for registering the first image to the second image based on the maximized image texture similarity.

Image acquisition logic 510 acquires two or more images of a material. In one embodiment, the two or more images are acquired at different times. In one embodiment, the material is a non-biological material. In another embodiment, the material is a region of biological tissue. In one embodiment, the images are 3D MRI images. In another embodiment, the images may be two dimensional images or non-MRI images. Image acquisition logic 510 also extracts image texture information from the two or more images. In one embodiment, members of the two or more images include a set of voxels and image texture information about the set of voxels.

Transformation logic 520 constructs an FEM of the region in the first image. In one embodiment, the FEM is a 3D FEM comprising a plurality of elements connected at nodes. The elements represent geometric shapes, including a tetrahedron, a hexahedron, or other geometric shape. A sparse stiffness matrix defines the interaction between nodes. Co-ordinates of nodes, displacement of nodes, and forces applied to the FEM are represented by vectors. Transformation logic 520 produces a deformed FEM by applying a non-zero force to the FEM. In one embodiment, transformation logic 520 applies a series of non-zero external forces to the surface of the FEM and calculates the displacement of nodes in the FEM caused by the series of non-zero external forces. In another embodiment, transformation logic 520 applies a series of non-zero forces to internal structures of the FEM. In still another embodiment, transformation logic 520 applies a series of non-zero forces to both the surface of the FEM and internal structures of the FEM. Transformation logic 520 also produces a deformed first image. The deformed first image is produced as a function of the solution to the deformed FEM. In one embodiment, transformation logic 520 employs a biconjugate gradient stabilized method to estimate the displacement of nodes in the FEM. In another embodiment, another method for solving for the displacements of the nodes in the FEM may be used. Estimating the displacement of nodes facilitates solving the FEM in a clinically relevant timeframe. Transformation logic 520 extracts a third image texture from the deformed first image. Upon determining that the similarity between the third image texture information and the second image texture information is maximized, transformation means 520 computes a transformation of the first image that achieves the deformed first image. The system 500 also includes a registration logic 530 that provides means for registering the first image to the second image. Registration logic 530 registers the two or more images using the transformation. In one embodiment, registering the two or more images may include updating a memory with a new image that represents the two aligned images.

Figure 6:
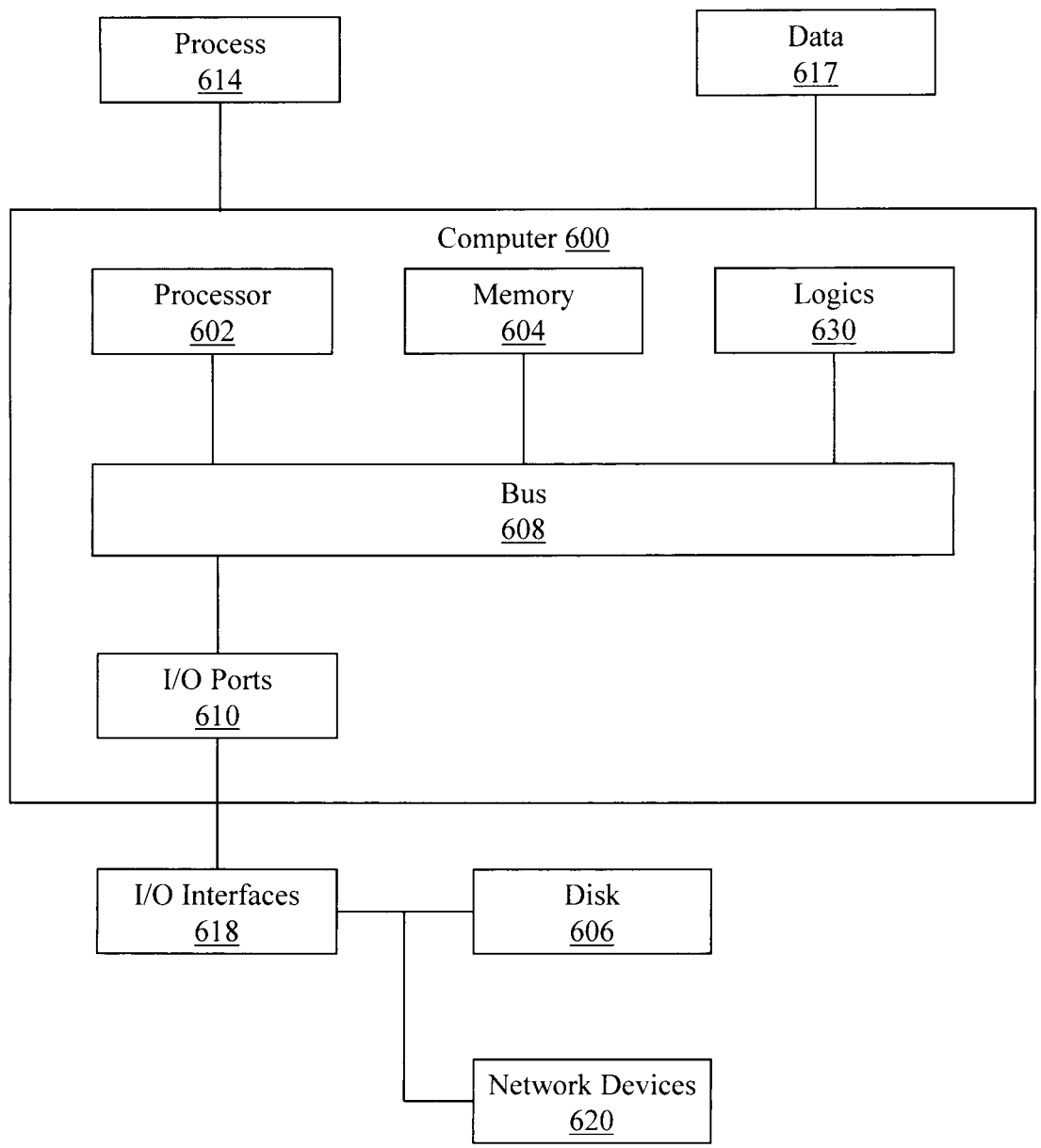
FIG. 6 illustrates an example computer in which example methods illustrated herein can operate.

FIG. 6 illustrates an example computer 600 in which example methods illustrated herein can operate and in which example logics may be implemented. In different examples computer 600 may be part of a MRI scanner or may be operably connectable to a MRI scanner that acquires MR images of a prostate or other region of tissue.

Computer 600 includes a processor 602, a memory 604, and input/output ports 610 operably connected by a bus 608. In one example, memory 604 may store registered images. In one example, computer 600 may include a set of logics 630 that performs a method of evaluating global deformations and local deformations in a prostate. In another example, the set of logics 630 may control the computer 600 to register a pre-EBRT image with a post-EBRT image. Registering the images may produce a new image that is stored as a new set of data. Thus, the set of logics 630, whether implemented in computer 600 as hardware, firmware, software, or a combination thereof may provide means (e.g., hardware, software, circuit) for receiving digitized image data, means (e.g., hardware, software, circuit) for performing a method of evaluating global deformations and local deformations in a prostate, an area, region, item, or volume, and means (e.g., hardware, software, circuit) for registering a pre-EBRT image with a post-EBRT image. In one embodiment, the digitized image data comprises a first image and a second image. The first image comprises a first set of voxels and image texture information about the first set of voxels. The second image comprises a second set of voxels and image texture information about the second set of voxels. In one embodiment, evaluating global deformations and local deformations in an organ, item, or volume comprises extracting image texture information from the first image and the second image, constructing an FEM of the organ, item, or volume represented in the first image, and deforming the FEM until the image texture similarity between the first image and the second image is maximized. In different examples, the set of logics 630 may be permanently and/or removably attached to computer 600.

Processor 602 can be a variety of various processors including dual microprocessor and other multi-processor architectures. Memory 604 can include volatile memory and/or non-volatile memory. A disk 606 may be operably connected to computer 600 via, for example, an input/output interface (e.g., card, device) 618 and an input/output port 610. Disk 606 may include, but is not limited to, devices like a magnetic disk drive, a tape drive, a Zip drive, a flash memory card, or a memory stick. Furthermore, disk 606 may include optical drives like a CD-ROM or a digital video ROM drive (DVD ROM). Memory 604 can store processes 614 or data 616, for example. Disk 606 and/or memory 604 can store an operating system that controls and allocates resources of computer 600.

Bus 608 can be a single internal bus interconnect architecture or other bus or mesh architectures. While a single bus is illustrated, it is to be appreciated that computer 600 may communicate with various devices, logics, and peripherals using other busses that are not illustrated (e.g., PCIE, SATA, Infiniband, 1394, USB, Ethernet).

Computer 600 may interact with input/output devices via I/O interfaces 618 and input/output ports 610. Input/output devices can include, but are not limited to, MRI scanners configured to acquire T2-weighted MRI images, a keyboard, a microscope, a microphone, a pointing and selection device, cameras, video cards, displays, disk 606, network devices 620, and other devices. Input/output ports 610 can include but are not limited to, serial ports, parallel ports, and USB ports.

Computer 600 may operate in a network environment and thus may be connected to network devices 620 via I/O interfaces 618, or I/O ports 610. Through the network devices 620, computer 600 may interact with a network. Through the network, computer 600 may be logically connected to remote computers. The networks with which computer 600 may interact include, but are not limited to, a local area network (LAN), a wide area network (WAN), and other networks.

In one example, a method may be implemented as computer executable instructions. Thus, in one example, a computer-readable storage medium may store computer executable instructions that if executed by a machine (e.g., computer) cause the machine to perform methods described or claimed herein including method 100 and method 300. While executable instructions associated with the listed methods are described as being stored on a computer-readable storage medium, it is to be appreciated that executable instructions associated with other example methods described or claimed herein may also be stored on a computer-readable storage medium. In different embodiments the example methods described herein may be triggered in different ways. In one embodiment, a method may be triggered manually by a user. In another example, a method may be triggered automatically.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage medium", as used herein, refers to a medium that stores instructions or data. "Computer-readable storage medium" does not refer to propagated signals. A computer-readable storage medium may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage medium may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Logic", as used herein, includes but is not limited to hardware, firmware, software in execution on a machine, or combinations of each to perform a function(s) or an action(s), or to cause a function or action from another logic, method, or system. Logic may include a software controlled microprocessor, a discrete logic (e.g., ASIC), an analog circuit, a digital circuit, a programmed logic device, a memory device containing instructions, and other physical devices. Logic may include one or more gates, combinations of gates, or other circuit components. Where multiple logical logics are described, it may be possible to incorporate the multiple logical logics into one physical logic. Similarly, where a single logical logic is described, it may be possible to distribute that single logical logic between multiple physical logics.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

To the extent that the phrase "one or more of, A, B, and C" is employed herein, (e.g., a data store configured to store one or more of, A, B, and C) it is intended to convey the set of possibilities A, B, C, AB, AC, BC, ABC, AAA, AAB, AABB, AABBC, AABBCC, (e.g., the data store may store only A, only B, only C, A&B, A&C, B&C, A&B&C, A&A&A, A&A&B, A&A&B&B, A&A&B&B&C, A&A&B&B&C&C). It is not intended to require one of A, one of B, and one of C. When the applicants intend to indicate "at least one of A, at least one of B, and at least one of C", then the phrasing "at least one of A, at least one of B, and at least one of C" will be employed.

While example systems, methods, and so on have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and so on described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable storage medium storing computer executable instructions that when executed by a computer cause the computer to perform a method associated with evaluating global deformations and local deformations in a prostate due to effects of External Beam Radiation Treatment (EBRT), the method comprising:
    accessing a three dimensional (3D) pre-EBRT magnetic resonance (MR) image of a prostate, where the 3D pre-EBRT image comprises a first set of voxels and first image texture information about the first set of voxels;
    accessing a 3D post-EBRT MR image of the prostate, where the 3D post-EBRT image comprises a second set of voxels and second image texture information about the second set of voxels;
    extracting the first image texture information from the 3D pre-EBRT image and extracting the second image texture information from the 3D post-EBRT image;
    constructing a finite element model (FEM) of the 3D pre-EBRT image, where the FEM discretizes structures of the prostate into elements of the FEM, where the elements of the FEM represent a geometric shape, where the elements of the FEM contain physical properties including elasticity or compressibility, and where the elements of the FEM are connected at nodes of the FEM;
    producing a deformation of the FEM by applying a series of non-zero external forces to the surface of the prostate represented by the FEM;
    calculating a transformation of the FEM, based at least in part, on the deformation, where the transformation is parameterized based on the series of non-zero external forces applied to the surface of the prostate;
    producing a deformed first image texture by deforming, as a function of the deformation of the FEM, the first image texture;
    determining, as a function of the transformation, a non-zero external force that maximizes an image texture similarity between the deformed first image texture and the second image texture; and
    upon determining the non-zero external force that maximizes the image texture similarity between the deformed first image texture and the second image texture, registering the 3D pre-EBRT image to the 3D post-EBRT image based, at least in part, on the transformation, where registering the 3D pre-EBRT image to the 3D post-EBRT image comprises spatially aligning the 3D pre-EBRT image with the 3D post-EBRT image.

2. The non-transitory computer-readable storage medium of claim 1, where the FEM is a 3D FEM, where the 3D FEM comprises a plurality of nodes N, where elements of the 3D FEM represent one of a tetrahedron or a hexahedron, where the tetrahedron is defined by four corner nodes, and where the hexahedron is defined by eight corner nodes.

3. The non-transitory computer-readable storage medium of claim 2, where interaction of nodes in three dimensions is defined by a 3N×3N matrix K, where K is a sparse, symmetrical matrix, and where a 3N×1 vector V represents co-ordinates of nodes in three dimensions, N being an integer.

4. The non-transitory computer-readable storage medium of claim 3, where the series of non-zero external forces is denoted by M, where a 3N×1 vector F represents the series of non-zero external forces M applied to a node in three dimensions, where M is less than or equal to the number of nodes N.

5. The non-transitory computer-readable storage medium of claim 4, where a 3N×1 vector U represents displacement of nodes in three dimensions by the series of non-zero external forces.

6. The non-transitory computer-readable storage medium of claim 5, where displacement of nodes in the FEM by the series of non-zero external forces is computed according to $U = K^{-1} \cdot F$, where U is estimated by minimizing $\|F - K \cdot U\|_2$.

7. The non-transitory computer-readable storage medium of claim 6, where the transformation is defined from the displacement of nodes, where nodes $S_c$ surrounding a voxel c in the first set of voxels are defined by corners of an element of the FEM, where the element contains the voxel c.

8. The non-transitory computer-readable storage medium of claim 7, where a transformation of the voxel c has 3M degrees of freedom, where the transformation of the voxel c is defined as a linear interpolation of the displacement of the nodes $S_c$, where the transformation of the voxel c is expressed as $$T(c) = c + \frac{\sum_{n \in S_c} \|c - v_n\|_2 \cdot u_n}{\sum_{n \in S_c} \|c - v_n\|_2},$$

where $u_n$ denotes displacement of a node n, and where $v_n$ denotes coordinates of a node n.

9. The non-transitory computer-readable storage medium of claim 8, where registering the 3D pre-EBRT image to the 3D post-EBRT image comprises calculating $T = \arg\max E(C_{Post}, T(C_{pre}))$, where $T(C_{Pre}) = \{C_{Pre}, f_{Pre}(T(c))\}$, where $C_{pre}$ is the 3D pre-EBRT image, $C_{Post}$ is the 3D post-EBRT image, $f_{Pre}$ is image texture information for a voxel, and where E denotes an image energy, where the image energy is defined as mutual information between a texture transformation of the 3D pre-EBRT image and the 3D post-EBRT image.

10. The non-transitory computer-readable storage medium of claim 9, the method comprising using a particle swarm optimizer to determine a series of non-zero external forces that maximize E.

11. The non-transitory computer-readable storage medium of claim 1, where producing a deformation of the FEM comprises applying a series of non-zero internal forces to internal structures of the prostate represented by the FEM.

12. A non-transitory computer-readable storage medium storing computer executable instructions that when executed by a computer cause the computer to perform a method, the method comprising:
    acquiring a 3D pre Radiation Treatment (RT) image of an anatomical structure and a 3D post-RT image of the anatomical structure;
    extracting first image texture information from the 3D pre-RT image;
    extracting second image texture information from the 3D post-RT image;

constructing a 3D finite element model (FEM) of the anatomical structure in the 3D pre-RT image;

deforming the FEM of the anatomical structure in the 3D pre-RT image to produce a deformation in the 3D pre-RT image that maximizes the similarity between the first image texture information and the second image texture information;

identifying an external force that maximizes the similarity of image texture information between the 3D pre-RT image and the 3D post-RT image;

constructing a transformation of the FEM that achieves the deformation, based, at least in part, on the external force; and registering the 3D pre-RT image with the 3D post-RT image, based at least in part, on the transformation.

13. The non-transitory computer-readable storage medium of claim 12, where the Radiation Treatment is an External Beam Radiation Treatment (EBRT).

14. The non-transitory computer-readable storage medium of claim 12, where the anatomical structure is a prostate.

15. An apparatus, comprising:
a processor;
a memory;
an input/output interface;
a set of logics that evaluates global deformations and local deformations in a material, where the global deformations and local deformations are caused by the effects of a treatment applied to the material; and
an interface to connect the processor, the memory, the input/output interface and the set of logics,
the set of logics comprising:
an image acquisition logic that acquires two or more images of the material, where the two or more images are acquired at different times, where the two or more images are 3D magnetic resonance (MR) images;
an image texture information logic that determines a texture property of the two or more images;
a Finite Element Model (FEM) transformation logic that computes a transformation for the two or more images using a 3D FEM, based, at least in part, on the texture property, and
a registration logic that registers the two or more images using the transformation.

16. The apparatus of claim 15, where the material is a cancerous tissue.

17. The apparatus of claim 15, where the treatment is an External Beam Radiation Treatment (EBRT).

18. The apparatus of claim 15, where members of the two or more images include a set of voxels and image texture information about the set of voxels.

19. The apparatus of claim 18, where the image texture information logic extracts the image texture information from the two or more images.

20. The apparatus of claim 19, where the FEM transformation logic:
constructs an FEM of the first image;
produces a deformed FEM by applying a non-zero force to the FEM;
calculates a displacement of nodes in the deformed FEM by generating a solution to the deformed FEM;
produces a deformed first image based on the solution to the deformed FEM;
extracts a third image texture information from the deformed first image; and
upon determining that the similarity between the third image texture information and the second image texture information is maximized,
determines which non-zero force maximizes the similarity, and
computes a transformation of the first image that achieves the deformed first image.

21. The apparatus of claim 20, where the FEM transformation logic employs a biconjugate gradient stabilized method to estimate the displacement of nodes in the FEM.

* * * * *